United States Patent [19]

Ogata et al.

[11] Patent Number: 4,873,292
[45] Date of Patent: Oct. 10, 1989

[54] ANTITHROMBOGENIC SYNTHETIC POLYMER AND PROCESS FOR ITS PREPARATION

[75] Inventors: Naoya Ogata; Kohei Sanui; Nobuhiko Yui; Kazunori Kataoka, all of Tokyo; Teruo Okano, Chiba; Yasuhisa Sakurai, Tokyo, all of Japan

[73] Assignee: Research Development Corporation of Japan, Tokyo, Japan

[21] Appl. No.: 154,003

[22] Filed: Feb. 9, 1988

Related U.S. Application Data

[63] Continuation-in-part of Ser. No. 814,974, Dec. 31, 1985, abandoned.

[51] Int. Cl.$^4$ ................... C08L 71/02; C08L 77/06
[52] U.S. Cl. .................... 525/408; 525/411; 525/420
[58] Field of Search ............. 525/408, 411, 420, 425, 525/437; 523/112

[56] References Cited

U.S. PATENT DOCUMENTS

| | | | |
|---|---|---|---|
| 3,044,987 | 7/1962 | Schaefgen et al. | 525/408 |
| 3,384,681 | 5/1968 | Kobayashi et al. | 525/411 |
| 3,746,683 | 7/1973 | Salyer et al. | 525/112 |
| 4,042,978 | 8/1977 | Jones et al. | 525/408 |
| 4,230,838 | 10/1980 | Foy et al. | 525/408 |
| 4,429,081 | 1/1984 | Mumcu et al. | 525/420 |

Primary Examiner—Patricia Short
Attorney, Agent, or Firm—Stephen F. K. Yee

[57] ABSTRACT

An antithrombogenic synthetic polymer has repeat structural units represented by the following structural formula consisting of portions I and II:

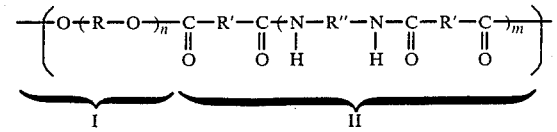

a microdomain structure composed of crystalline phases and amorphous phases, each phase having an average size of 5 to 10 nm, and a molecular weight in the range of about 10,000 to about 300,000. The polymer exhibits little adhesion of blood platelets thereto, an excellent antithrombogenic property and a sufficient mechanical strength.

8 Claims, 3 Drawing Sheets

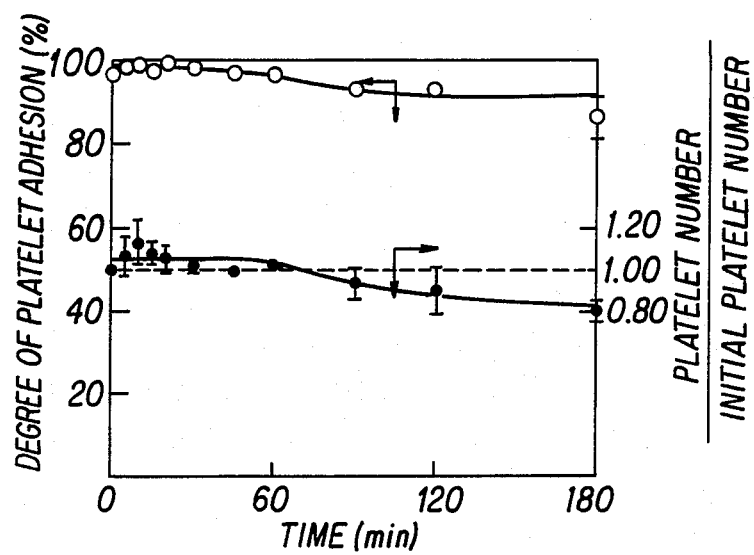
FIG. 1 Non-AV Shunt (Control)
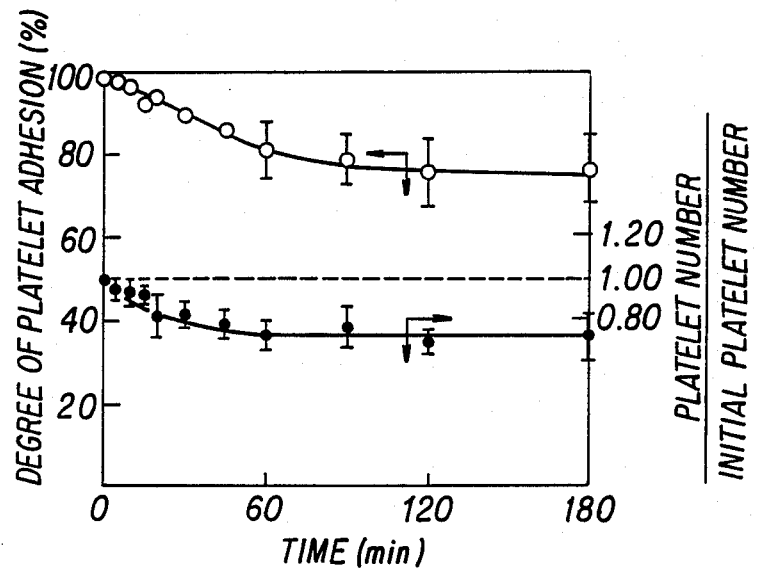
FIG. 2 Polyetherurethane AV Shunt

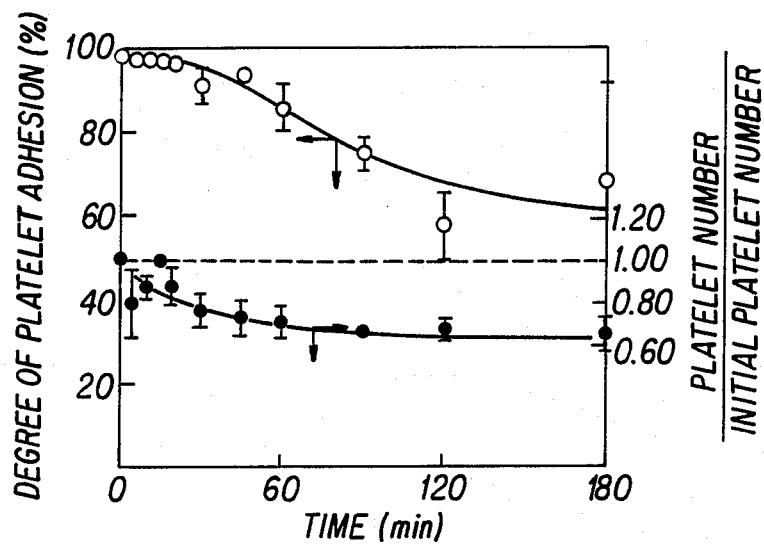
FIG. 3 PHEMA Homopolymer AV Shunt
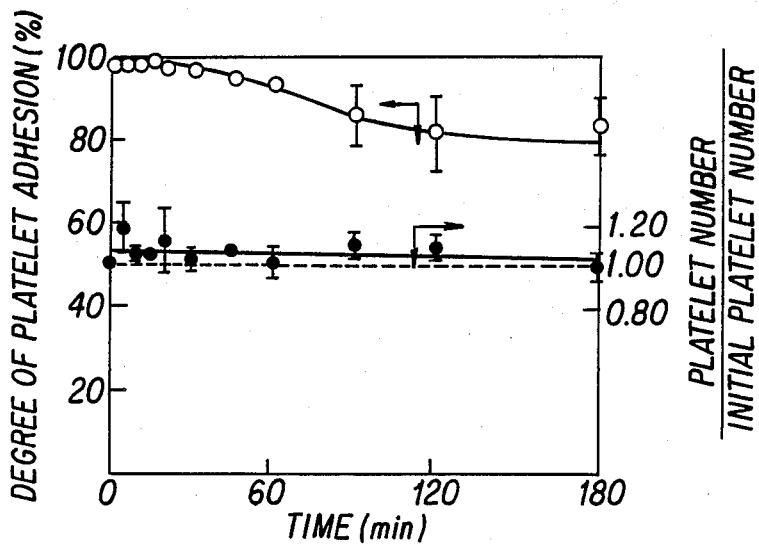
FIG. 4 PPO-segmented Ny. 610 AV Shunt

ANTITHROMBOGENIC SYNTHETIC POLYMER AND PROCESS FOR ITS PREPARATION

CROSS REFERENCE TO RELATED APPLICATION

This application is a continuation-in-part of application Ser. No. 814,974, filed on Dec.31, 1985, now abandoned.

BACKGROUND OF THE INVENTION

1. Technical Field

The present invention relates to a novel antithrombogenic synthetic polymer, and more particularly to an antithrombogenic block copolymer composed of crystalline polymer chains and amorphous polymer chains.

2. Background Information

The need for development of synthetic polymers having excellent antithrombogenic properties has existed in a wide range of biomedical fields, including artificial blood vessels, artificial organs, bioseparators, medical materials and instruments, and the like.

At present, the short-term use of artificial blood vessels or artificial kidneys during operations is increasing, and the utilization of artificial hearts or bioseparators has been partly attempted. However, the artificial blood vessels or the artificial kidneys are used together with the so-called anticoagulants, such as heparin and the like. Accordingly, when they are used for a long period of time, and further, when they are implanted in human bodies, there are unsolved problems concerning the affinity of their materials with blood or tissues or the biological stability of their materials. Under present conditions, any material which affords full satisfaction to these problems has not yet been obtained.

Particularly, in the case of artificial blood vessels and the like, which are used in contact with blood, the antithrombogenic property of the materials is the most important problem, and an urgent solution is necessary.

SUMMARY OF THE INVENTION

It is therefore a primary object of the present invention to provide a synthetic polymer having an excellent antithrombogenic property.

For the purpose of achieving this object, the inventors have studied various adhesion phenomena of blood platelets to the surfaces of materials used in contact with blood. As a result, it has been found that the problems described above are solved by a polymer having both polyether units and polyamide units, thus arriving at the present invention.

In accordance with the present invention, there is provided an antithrombogenic synthetic polymer having repeat structural units represented by the following structural formula consisting of portions I and II:

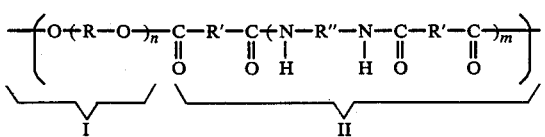

where R is a straight-chain or branched-chain alkylene group containing from 2 to 4 carbon atoms, R' is a straight-chain alkylene group containing from 2 to 10 carbon atoms, a cyclohexyl group of an aromatic ring group such as a phenyl group, a diphenylether group or a diphenylmethane group, R" is a straight-chain or branched-chain alkylene group containing from 1 to 10 carbon atoms, a cyclohexyl group or an aromatic ring group such as a phenyl group, a diphenylether group or a diphenylmethane group, n is an integer in the range of 13 to 180, preferably in the range of 13 to 60, and m is an integer in the range of 1 to 400, preferably in the range of 1 to 120. The polymer has a microdomain structure composed of crystalline phases and amorphous phases, each phase having an average size of 5 to 10 nm, and a molecular weight in the range of about 10,000 to about 300,000, preferably in the range of 20,000 to 100,000.

BRIEF DESCRIPTION OF THE DRAWINGS

FIGS. 1–5 show test data for the variation with time of platelet concentration and degree of platelet adhesion, for different materials tested.

DESCRIPTION OF THE PREFERRED EMBODIMENTS

Figure 5:
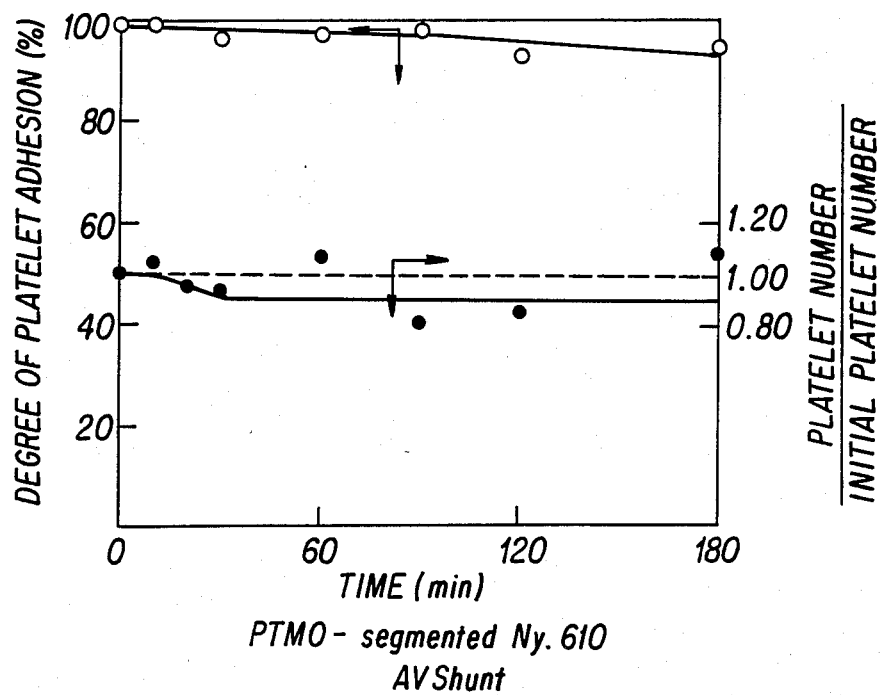

Portion I of the structural formula represents a repeat unit of a polyesther, and portion II represents a repeat unit of a polyamide. Portions I and II are connected to each other by an ester linkage, but they may be directly connected to each other by an amide linkage.

In portion I of the structural formula, R is a straight-chain or branched-chain alkylene group containing from 2 to 4 carbon atoms, such as an ethylene group, an isopropylene group or a tetramethylene group, and n is in the range of 13 to 180, preferably from 13 to 60, although n is not particularly limited.

The crystal structure of portion II of the structural formula, being namely a polyamide, changes with the number of carbon atoms of R', containing from 2 to 10 carbon atoms, preferably from 4 to 8 carbon atoms, and R", containing from 1 to 10 carbon atoms, preferably from 2 to 7 carbon atoms.

While the combination of R' and R" is not particularly limited, it has been confirmed that it is preferable for preparing the crystalline-amorphous microdomain structure that the polyamide portion (polymer block), represented by portion II of the structural formula, have a high crystallinity, and also preferable that R' and R" are straight-chain hydrocarbon groups with even carbon number, respectively, such that R' is an octamethylene group and R" is a hexamethylene group.

The polymer is characterized by a microdomain structure composed of crystalline phases and amorphous phases, each phase having an average size of 5 to 10 nm. This size is variously changeable with the chemical structures of the polymerization units in portions I and II of the structural formula, or with the quantitative relationship between the polymerization units of portions I and II in the polymer.

The average size of the crystalline phases was determined by the use of a wide angle x-ray scattering meter. The average size of the amorphous phases was determined by subtracting the average size of the crystalline phases previously measured from the average repeat size of the crystalline phases and the amorphous phases measured with a small angle x-ray scattering meter.

Although m is not particularly limited, it is in the range of 1 to 400, preferably in the range of 1 to 120.

The quantitative relationship between the polymer blocks of the polymerization units in portions I and II of the structural formula is not particularly limited, but it is preferable that ferably from about 10 to about 47% by weight, and most preferably from about 13 to about 27% by weight.

While the antithrombogenic synthetic polymer of the present invention can be synthesized by various processes, it is usually produced by reacting a polyether with a dicarboxylic acid halide to synthesize a prepolymer in which acid halide groups are introduced to both ends of the polyether indicated by portion I of the structural formula described above, and thereafter reacting the prepolymer with a dicarboxylic acid halide and a diamine to polycondense them, in order to form portion II of the structural formula. The polymer may also be produced by reacting a polyether having acid halide groups or amino groups at both ends thereof, with a dicarboxylic acid halide and a diamine to polycondense them. Further, the polymer may be produced by first synthesizing portion II of the structural formula having amino groups or acid halide groups at both ends thereof by the reaction of a dicarboxylic acid with a diamine, and thereafter reacting it with portion I of the structural formula synthesized by the process described above. The synthetic polymer of the present invention thus produced is a multi-block copolymer.

The polyether which is the raw material compound mentioned above includes, for example poly(ethylene oxide), poly(propylene oxide), poly(tetramethylene oxide) and the like.

As the dicarboxylic acid halide, there can be mentioned a dicarboxylic acid chloride, a dicarboxylic acid bromide, a dicarboxylic acid fluoride and a dicarboxylic acid iodide, and especially a dicarboxylic acid chloride is preferable.

The dicarboxylic acid chloride includes adipic acid chloride, suberic acid chloride, sebacic acid chloride, terephthalic acid chloride, and the like, and the diamine includes 1,2 ethylenediamine, 1,2-propylenediamine, 1,3-propylenediamine, 1,4-tetramethylenediamine, 1,5 pentamethylenediamine, 1,6 hexamethylenediamine, 1,7 heptamethylenediamine, and the like.

The antithrombogenic synthetic polymer of the present invention has several desirable characteristics which make it suitable for use in artificial organs, including artificial blood vessels, artificial kidneys, artificial hearts, and the like, which are employed in contact with blood, and for medical materials and instruments, such as absorbents for biological components, carriers for sustained release preparations, adhesive materials for living tissue, injectors, blood bags, catheters and the like.

First, the synthetic polymer of the present invention shows a very excellent antithrombogenic property. That is to say, it is observed that the adhesion of blood platelets to the polymer surface is extremely low and deformation of adhered blood platelets does not occur. Also, with respect to granulocytes and lymphocytes, similar results are obtained.

Secondly, this synthetic polymer shows a high mechanical strength and elasticity because a portion II of the structural formula. Accordingly, the high stability of this polymer can be appreciated when it has been implanted in vivo for a long period of time, in addition to the expectation of physical properties necessary for manufacturing artificial organs.

Thirdly, this synthetic polymer has a softness which is necessary in clinical use as artificial organs, together with the characteristics of portion II of the structural formula described above, because of portion I of the structural formula.

Fourthly, the microdomain structure composed of crystal structure in the materials can be controlled by variation of the quantitative relationship between portions I and II of the structural formula, and the antithrombogenic property of the material can be easily improved by this microdomain structure.

Methods for using the synthetic polymer of the present invention as antithrombogenic materials will hereinafter be described.

When this synthetic polymer is used for artificial blood vessels, artificial kidneys, artificial hearts, absorbents for biological components, and carriers for sustained release preparations, it can be shaped in the desired forms. For example, when it is desired to cast the polymer in a film form, the polymer can be casted in a desired thickness by a technique in which the polymer dissolved in a solvent is used. Further, the polymer can be molded in the other forms by a technique of plasticizing with heat and the like.

Furthermore, the functions of the present invention can also be shown by the technique in which this synthetic polymer is applied onto conventional polymers, without using this synthetic polymer for the structural members as it is. The synthetic polymer of the present invention attains superiority over natural materials in the shaping thereof.

The synthetic polymer of the present invention has both the portion I, namely the polyether portion, and the portion II, namely the polyamide portion, of the structural formula. The polymer has, therefore, the microdomain structure of a crystal-line-amorphous type, which structure has the softness of the polyether (amorphous) and the rigidity of the polyamide (crystalline). As a consequence, the polymer not only has excellent molding capability, processability and durability, but also improved antithrombogenic property.

The present invention will now be described further with reference to the following examples that by no means limit the scope of the invention.

EXAMPLE 1

Poly(propylene oxide) having a number average molecular weight of about 3,000 and an excess amount of sebacoyl chloride were reacted with each other under an atmosphere of nitrogen, at a temperature of 80° to 90° C., for 6 hours, to synthesize poly(propylene oxide) having acid chloride groups at both ends thereof. This reaction product was dissolved in chloroform after being cooled to room temperature, and the interfacial polymerization was carried out by stirring it together with a 1,6 hexamethylenediamine-sodium hydroxide solution at high speed. Thus, the synthetic polymer was obtained having the following repeat structural unit:

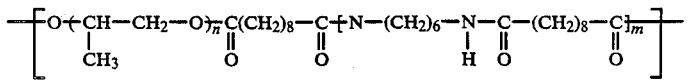

wherein n was 51 and m was 33. The molecular weight of this polymer was about 70,000, and the average sizes of the crystalline phases and amorphous phases were 6.5 nm and 5.1 nm, respectively.

The poly(propylene oxide) content of this synthetic polymer was 25%.

EXAMPLE 2

Poly(propylene oxide) having a number average molecular weight of about 3,000 and an excess amount of sebacoyl chloride were reacted with each other under an atmosphere of nitrogen, at a temperature of 80° to 90° C., for 6 hours, to synthesize poly(propylene oxide) having acid chloride groups at both ends thereof. This reaction product was dissolved in chloroform after being cooled to room temperature, and the interfacial polymerization was carried out by stirring it together with a 1,2 ethylenediamine-sodium hydroxide solution at high speed. Thus, the synthetic polymer was obtained having the following repeat structural unit:

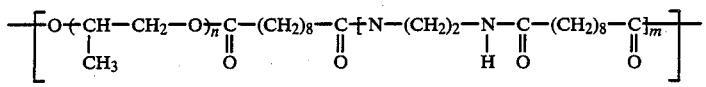

wherein n was 51 and m was 90. The molecular weight of this polymer was about 25,000, and the average sizes of the crystalline phases and amorphous phases were 6.1 nm and 5.8 nm, respectively.

The poly(propylene oxide) content of this synthetic polymer was 13%.

EXAMPLE 3

Poly(tetramethylene oxide) having a number average molecular weight of about 980 and an excess amount of sebacoyl chloride were reacted with each other under an atmosphere of nitrogen, at a temperature of 80° to 90° C., for 6 hours, to synthesize poly(tetramethylene oxide) having acid chloride groups at both ends thereof. This reaction product was dissolved in chloroform after being cooled to room temperature, and the interfacial polymerization was carried out by stirring it together with a 1,6 hexamethylenediamine-sodium hydroxide solution at high speed. Thus, the synthetic polymer was obtained having the following repeat structural unit;

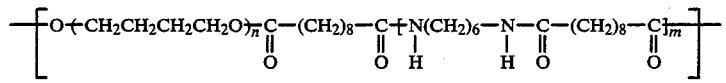

wherein n was 13 and m was 9. The molecular weight of this polymer was about 65,000, and the average sizes of the crystalline phases and amorphous phases were 6.7 nm and 4.9 nm, respectively.

The poly(tetramethylene oxide) content of this synthetic polymer was 27%.

Structural identification of the synthetic polymers obtained in Examples 1 through 3 was carried out as follows. The formation of the polyether having the acid chloride groups at both ends thereof synthesized by the reaction of the polyether with sebacoyl chloride was identified by the infrared absorption spectrum (IR). That is to say, by the reaction, the absorption at 3470 cm$^{-1}$ caused by the end hydroxyl group of the polyether disappeared, and instead the absorption at 1730 cm$^{-1}$ caused by the ester group was observed.

The synthesis of the synthetic polymer by the reaction of the product described above with the diamine was identified by the infrared absorption spectrum (IR). Namely, by the reaction, the absorption at 1800 cm$^{-1}$ caused by the acid chloride disappeared, and instead the absorptions at 1540 cm$^{-1}$, 1640 cm$^{1-}$ and 3300 cm$^{-1}$ caused by the amide group were observed. The absorption at 1730 cm$^{-1}$ caused by the ester group corresponding to the connecting part of portion I and portion II of the structural formula was observed as it was.

Because this synthetic polymer was purified by the use of methanol, which was a good solvent therefor, it was concluded that this synthetic polymer had the prescribed structure.

COMPARATIVE EXAMPLE

Glass beads having the size in the range of 48 to 60 meshes were washed with a potassium hydroxide-sodium hydroxide-ethanol aqueous solution and water. Twenty grams of the washed glass beads were immersed in 20 ml of m-cresol solutions in which the polymers prepared in Examples 1 to 3 were dissolved in an amount of 40 mg, respectively.

After being stirred at room temperature for one hour, they were filtered and dried, under reduced pressure at 60° C., for 48 hours. By using the glass beads thus coated with the polymers, the following experiments were carried out.

The glass beads described above were densely packed in polyvinyl chloride tubes of 3 mm diameter and 10 cm length, and fresh blood collected from the jugular being of a mongrel adult dog was passed therethrough at a flow rate of 0.4 ml/min for one minute.

With respect to the polymers prepared in Examples 1 through 3, only 20%, 15% and 25%, respectively, of the whole blood platelets in the blood adhered to the polymer-coated beads.

On the contrary, when the experiments were carried out under the same conditions, except that the polymers prepared in Examples 1 and 3 were replaced with nylon 610, which was the material represented by portion II of the structural formulas thereof, and the polymer prepared in Example 2 was replaced with nylon 210, which was the material represented by portion II of the structural formula thereof, about 40% and 30% of the whole blood platelets in the blood adhered to the nylon 610 and nylon 210 coated beads, respectively. The amounts of the blood platelets which adhered to the beads coated with polymers prepared in Examples 1 through 3 were only about half of those which adhered to the beads coated with nylons.

Further, the blood platelets which adhered to the surfaces of nylons 610 and 210 were aggregated, and marked deformations were observed. In case of the polymers prepared in Examples 1 through 3, however, the adhered blood platelets retained their original shapes.

EXAMPLES 4–8

Various polymers of polypropylene oxide-segmented nylon 610 (PPO-NY.610) having the following repeat

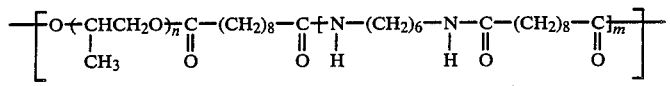

structural units were prepared and identified as Examples 4–8:

wherein
n is 51 and m is 118 (Example 4)
n is 51 and m is 33 (Example 5)
n is 34 and m is 16 (Example 6)
n is 51 and m is 12 (Example 7)
n is 34 and m is 2 (Example 8)

The molecular weight of the polymers of Examples 4–8 was in the range of 70,000–100,000.

The platelet adhesion characteristics of Nylon 610 as well as the polypropylene oxide-segmented polymers of Examples 4–8 were determined in the same manner as described above, with the results of such tests set forth below.

TABLE 1

| Polymer | Wt. % of PPO in Copolymer (%) | Amount of Adhering Platelets (%) |
|---|---|---|
| Nylon 610 | 0 | 38.5 ± 4.30 |
| Example No. 4 | 10 | 25.9 ± 2.84 |
| Example No. 5 | 25 | 19.4 ± 3.64 |
| Example No. 6 | 31 | 22.9 ± 2.99 |
| Example No. 7 | 47 | 27.5 ± 4.02 |
| Example No. 8 | 78 | 33.2 ± 1.42 |

EXAMPLES 9–11

Various polymers comprised of polypropylene oxide-segmented aromatic polyamide were prepared as follows. Poly(propylene oxide)-segmented aromatic polyamide was synthesized by an interfacial polycondensation method. Poly(propylene oxide) with a molecular weight of 3,000 was reacted with terephthaloyl chloride in monochlorobenzene, at 130°–140° C., for 3 hours, with stirring. The reaction mixture was quickly cooled to room temperature and the solution rapidly poured, with vigorous stirring, into a blender containing an aqueous solution of 1,6-hexanediamine and sodium hydroxide. After 5 minutes of stirring, the precipitate was collected, poured into methanol, followed by stirring overnight. The sample was dried at 40° C., in vacuo, for 24 hours, to yield a white powder.

Ester and amide linkages were identified by IR spectroscopy, and the weight fraction of poly(propylene oxide) in the copolymer calculated by elemental analysis.

The various segmented polymers which were produced are identified below as Examples 9–11:

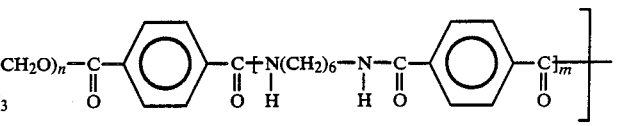

wherein
n is 51 and m is 69 (Example 9)
n is 51 and m is 64 (Example 10)
n is 51 and m is 18 (Example 11)

The molecular weight of polymer Examples 9–11 was in the range of 70,000–100,000.

The platelet adhesion characteristics of the noted polyamide as well as the polypropylene oxide-segmented polymers of Examples 9–11 were determined in the same manner as described above, with the results of such tests set forth below.

TABLE 2

| Polymer | Wt. % of PPO in Copolymer (%) | Amount of Adhering Platelets (%) |
|---|---|---|
| aromatic polyamide | 0 | 45 ± 5 |
| Example No. 9 | 15 | 7 ± 2 |
| Example No. 10 | 16 | 14 ± 5 |
| Example No. 11 | 41 | 24 ± 5 |

All data in Tables 1 and 2 are calculated as the mean, ±standard error of the mean.

Evaluation of Platelet Adhesion

Coating of various condensation polymers onto glass beads was carried out by using the following solvent evaporation technique. The glass beads (40–60 mesh) were immersed in 0.5 wt. % solution of the various polymers in m-cresol. Then the contents were poured into a microfilter mounted in a suction funnel to separate the glass beads from the solution. The glass beads were dried, in vacuo, at 60° C., for 48 hours. Confirmation of polymer coating was made by scanning electron microscopic observation and iodine adsorption from 5% iodine-aqueous solution.

The various polymers evaluated include PPO-NY.610 (Example 1) and PTMO-NY.610 having the following formula:

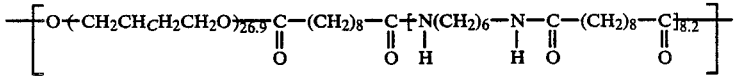

wherein portion I comprises 44% of the polymer.

1 g of polymer-precoated glass beads was packed in a tubing of poly(vinyl chloride) and was subjected to the following platelet adhesion test. 3 cm³ of fresh blood was collected from a jugular vein of a mongrel dog with a disposable syringe without any anticoagulant and was immediately passed through the column packed with the glass beads for 1 min., at a flow rate of 1.2 cm³/min., using a Precidol model 5003 infusion pump. The eluted blood was collected, along with the primed saline, in a sampling bottle containing 0.1 cm$^3$ of sodium citrate solution as an anticoagulant. The number of platelets in the fresh and eluted blood were counted, with the results shown in Table 3 below.

TABLE 3

Platelet Adhesion on Condensation Polymers

| Polymer | Amt. of Adhered Platelets % ($\pm$ S.E.) |
|---|---|
| PPO-NY.610 (Example 1) | 22.6 $\pm$ 3.3 |
| PTMO-NY.610 | 15.1 $\pm$ 3.3 |
| Nylon 610 homopolymer (comparison) | 35.5 $\pm$ 5.9 |
| Glass (control) | 23.7 $\pm$ 2.1 |

Blood-Contacting Properties of PTMO-Segmented Nylon 610

Acute in vivo antithrombogenicity of PTMO-segmented nylon 610 copolymer was evaluated by constructing an arteriovenous (AV) shunt in a Japanese white rabbit by surgically inserting a polymer-precoated segmented polyurethane (SPU) tubing into the right carotid artery and the left jugular vein.

For the acute experiment, a specific volume of fresh blood was collected at prescribed times through a catheter in a femoral artery to estimate changes in the number and adhesiveness of circulating platelets with the tubing-implanted time. Poly(2-hydroxyethyl methacrylate) (PHEMA) and polyetherurethane tubings were used as the references samples in these experiments.

It is known that normal platelets adhere on the polystyrene surface, but activated or damaged platelets show a reduction in adhesiveness. In this experiment, the degree or amount of platelet adhesion was determined by passing the blood through a column packed with polystyrene-precoated glass beads, in the manner described above. The number of platelets in the sample blood and the eluted blood were counted. The degree of platelet adhesion (A) was calculated according to the following equation:

$$(A) = \left(1 - \frac{\text{number of eluted platelets}}{\text{number of fed platelets}}\right) \times 100\%$$

The relative number (B) of platelets deposited on the copolymer-coated AV shunt was calculated according to the following equation:

$$(B) = \frac{\text{platelet number (sample)}}{\text{initial platelet number}}$$

The changes in the relative number and adhesiveness of circulating platelets with the length of implant time of the tubings are shown in FIGS. 1-5 for the tubing materials noted above. Here the adhesiveness of circulating platelets was estimated as one of the platelet functions in vivo. Polyetherurethane and PHEMA tubings showed relatively large decreases in the relative number and adhesiveness of circulating platelets compared with the control, that is, only with the cannulation of poly(vinyl chloride) catheter. These results indicate the reduction of the function and number of platelets due to their contact with or deposition on these polymer surfaces. On the other hand, the relative number and adhesiveness of circulating platelets for PTMO-segmented Ny 610 was almost the same level as the control. These results strongly support the conclusion that a PTMO-segmented Ny 610 surface eliminates the activation process of absorbed platelets.

In FIGS. 1-5, the open circles represent platelet adhesion data points, while the dark circles represent relative number data points.

The significance of the results shown in FIGS. 1-5 can be better appreciated from the following brief discussion of the blood platelet activation phenomenon.

Platelet adhesion and subsequent activation on foreign surfaces are major events which facilitate catastrophic thrombosis. The activation process for a blood platelet, or the interaction of the platelet with a material surface, consists of two distinct but sequential stages.

The first stage is physio-chemical adsorption wherein the interaction of the platelet with the material surface is driven by a physio-chemical force. Thus, surfaces which eliminate or minimize this physio-chemical adsorption of platelets can be expected to be non-thrombogenic.

The first stage is followed by the second stage, which may be defined as "contact-induced activation". The most distinctive feature of platelets from that of such non-vital particles as polymer latex is the existence of this activation stage. In the contact-induced activation stage, a reorganization occurs of the platelet's intracellular cytoskeletal components, i.e., the microfilaments and microtubules, due to the change in the energymetabolism of the platelets.

Thus, activated platelets undergo a sequence of events, including shape change, releasing of intracellular granules, and aggregation, which lend impetus to thrombosis formation.

Even though a limited number of adsorbed platelets are activated, they will significantly facilitate the thrombosis by gathering circulating platelets to form aggregates, and accelerate the coagulation cascade through the release of platelet factor 3.

In the tests of FIGS. 1-5, the degree of platelet adhesion to the polystyrene surface was monitored. As noted above normal platelets will adhere onto the polystyrene, while activated, or damaged, platelets show a reduction in such adhesion. Thus, in this experiment the higher the degree of platelet adhesion the better since this represents fewer damaged platelets. FIG. 1 (the control material) and FIGS. 4 and 5 (materials of the present invention) show the better results, while FIGS. 2 and 3 (the comparison materials) show the worst results.

The results of these tests clearly demonstrate that platelets are less likely to be activated or damaged with materials of the present invention than when the present invention is not used.

It should be noted that while the data in Tables 1-3 and in FIGS. 1-5 include platelet adhesion, these experiments measure different factors relating to thrombosis. The results in Tables 1-3 illustrate the reduced adhesion of platelets to the surfaces of the polymeric materials of the present invention, in comparison with other materials which may be used in contact with blood. In these results, a lower value of platelet adhesion represents a better antithrombogenic material. In the results shown in FIG. 1-5, a higher value of platelet adhesion represents a better contithrombogenic material since a totally different factor is being monitored, which is the number of activated, or damaged, platelets. Here, a higher platelet adhesion value represents fewer activated platelets and thus a material having better antithrombogenic property since it is less likely to damage the platelets.

What is claimed is:

1. An antithrombogenic synthetic polymer having repeat structural units represented by the following structural formula consisting of portions I and II:

$$-\left[O+R-O\right)_n \underset{\underset{O}{\|}}{C}-R'-\underset{\underset{O}{\|}}{C}+\underset{\underset{H}{|}}{N}-R''-\underset{\underset{H}{|}}{N}-\underset{\underset{O}{\|}}{C}-R'-\underset{\underset{O}{\|}}{C}\Big)_m\right]-$$
$$\underbrace{\hphantom{O+R-O)_n}}_{I} \underbrace{\hphantom{C-R'-C+N-R''-N-C-R'-C)_m}}_{II}$$

where R is a straight-chain or branched-chain alkylene group containing from 2 to 4 carbon atoms, R' is a straight-chain alkylene group containing from 2 to 10 carbon atoms or an aromatic ring group, R" is a straight-chain or branched-chain alkylene group containing up to 10 carbon atoms, n is an integer which ranges from 13 to 180, and m is an integer ranging from 1 to 400, said polymer having a microdomain structure composed of crystalline phases and amorphous phases, each phase having an average size of between 5 to 10 nm, and the molecular weight of said polymer being in the range of about 10,000 to about 300,000, the portion I being present in an amount ranging from about 13% to about 27% by weight of the polymer.

2. An antithrombogenic synthetic polymer according to claim 1, wherein said polymer has repeat structural units represented by the following structural formula:

$$-\left[O+\underset{\underset{CH_3}{|}}{CH}-CH_2-O\right)_{51}\underset{\underset{O}{\|}}{C}+CH_2)_8-\underset{\underset{O}{\|}}{C}+\underset{\underset{H}{|}}{N}-(CH_2)_6-\underset{\underset{H}{|}}{N}-\underset{\underset{O}{\|}}{C}-(CH_2)_8-\underset{\underset{O}{\|}}{C}\Big]_{133}-$$

the molecular weight of said polymer being about 70,000, the average size of said crystalline phases being about 6.5 nm, and the average size of said amorphous phases being about 5.1 nm, said portion I being present in an amount of about 25%.

3. An antithrombogenic synthetic polymer according to claim 1, wherein said polymer has repeat structural units represented by the following structural formula:

$$-\left[O+\underset{\underset{CH_3}{|}}{CH}-CH_2-O\right)_{51}\underset{\underset{O}{\|}}{C}+CH_2)_8-\underset{\underset{O}{\|}}{C}+\underset{\underset{H}{|}}{N}-(CH_2)_2-\underset{\underset{H}{|}}{N}-\underset{\underset{O}{\|}}{C}-(CH_2)_8-\underset{\underset{O}{\|}}{C}\Big]_{190}-$$

the molecular weight of said polymer being about 25,000, the average size of said crystalline phases being about 6.1 nm, and the average size of said amorphous phases being about 5.8 nm, said portion I being present in an amount of about 13%.

4. An antithrombogenic synthetic polymer according to claim 1, wherein said polymer has repeat structural units represented by the following structural formula:

$$-\left[O+CH_2CH_2CH_2CHO\right)_{13}\underset{\underset{O}{\|}}{C}-(CH_2)_8-\underset{\underset{O}{\|}}{C}+\underset{\underset{H}{|}}{N}(CH_2)_6-\underset{\underset{H}{|}}{N}-\underset{\underset{O}{\|}}{C}-(CH_2)_8-\underset{\underset{O}{\|}}{C}\Big]_{19}-$$

the molecular weight of said polymer being about 65,000, the average size of said crystalline phases being about 6.7 nm, and the average size of said amorphous phase being about 49 nm, said portion I being present in an amount of about 27%.

5. An antithrombogenic synthetic polymer having repeat structural units represented by the following structural formula consisting of portions I and II:

$$-\left(O+R-O\right)_n \underset{\underset{O}{\|}}{C}-R'-\underset{\underset{O}{\|}}{C}+\underset{\underset{H}{|}}{N}-R''-\underset{\underset{H}{|}}{N}-\underset{\underset{O}{\|}}{C}-R'-\underset{\underset{O}{\|}}{C}\Big)_m\right)$$
$$\underbrace{\hphantom{O+R-O)_n}}_{I} \underbrace{\hphantom{C-R'-C+N-R''-N-C-R'-C)_m}}_{II}$$

wherein R is a straight-chain or branched-chain alkylene group containing from 2 to 4 carbon atoms, R" is a straight-chain alkylene group containing from 2 to 10 carbon atoms, R" is a straight-chain or branched-chain alkylene group containing up to 10 carbon atoms, n is an integer which ranges from 13 to 180, and m is an integer ranging from 1 to 400, said polymer having a microdomain structure composed of crystalline phases and amorphous phases, each phase having an average size of 5 to 10nm, and the molecular weight of said polymer being in the range of about 10,000 to about 300,000, the portion I being present in an amount ranging from about 13 to about 27% by weight of the polymer, which polymer is produced by the process comprising the steps of reacting a polyether with a dicarboxylic acid halide to obtain a prepolymer in which acid halide groups are introduced to both ends of the polyether indicated by the portion I of said structural formula, and thereafter polycondensing said acid halide compound prepolymer with a dicarboxylic acid halide and a diamine to give the portion II of said structural formula.

6. An antithrombogenic synthetic polymer according to claim 5, wherein said polymer has repeat structural units represented by the following structural formula:

$$-\left[O+\underset{\underset{CH_3}{|}}{CH}-CH_2-O\right)_{51}\underset{\underset{O}{\|}}{C}+CH_2)_8-\underset{\underset{O}{\|}}{C}+\underset{\underset{H}{|}}{N}-(CH_2)_6-\underset{\underset{H}{|}}{N}-\underset{\underset{O}{\|}}{C}-(CH_2)_8-\underset{\underset{O}{\|}}{C}\Big]_{133}-$$

the molecular weight of said polymer being about 70,000, the average size of said crystalline phases being about 6.5 nm, and the average size of said amorphous phases being about 5.1 nm, said portion I being present in an amount of about 25%.

7. An antithrombogenic synthetic polymer according to claim 5, wherein said polymer has repeat structural units represented by the following structural formula:

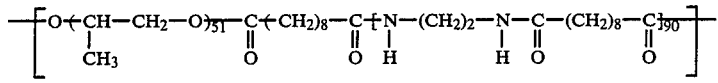

the molecular weight of said polymer being about 25,000, the average size of said crystalline phases being about 6.1 nm, and the average size of said amorphous phases being about 5.8 nm, said portion I being present in an amount of about 13%.

8. An antithrombogenic synthetic polymer according to claim 5, wherein said polymer has repeat structural units represented by the following structural formula:

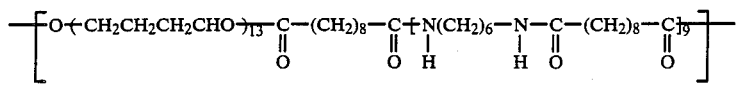

the molecular weight of said polymer being about 65,000, the average size of said crystalline phases being about 6.7 nm, and the average size of said amorphous phases being about 4.9 nm, said portion I being present in an amount of about 27%.

* * * * *